US00PP27357P2

(12) United States Plant Patent
Bean

(10) Patent No.: US PP27,357 P2
(45) Date of Patent: Nov. 8, 2016

(54) ***AGAPANTHUS* PLANT NAMED 'WP001'**

(50) Latin Name: ***Agapanthus* hybrid**
Varietal Denomination: WP001

(71) Applicant: Charles Andrew de Wet, Johannesburg (ZA)

(72) Inventor: Quinton Bean, Johannesburg (ZA)

(73) Assignee: Charles Andrew de Wet, Johannesburg (ZA)

( * ) Notice: Subject to any disclaimer, the term of this patent is extended or adjusted under 35 U.S.C. 154(b) by 79 days.

(21) Appl. No.: 14/545,012

(22) Filed: Mar. 16, 2015

(51) Int. Cl.
*A01H 5/02* (2006.01)

(52) U.S. Cl.
USPC ..... Plt./398

(58) Field of Classification Search
USPC ..... Plt./398
See application file for complete search history.

*Primary Examiner* — Anne Grunberg
(74) *Attorney, Agent, or Firm* — Penny J. Aguirre

(57) ABSTRACT

A new cultivar of *Agapanthus*, 'WP001', that is characterized by its fast growing and fast multiplying growth habit, its inflorescences that form dense umbels of flowers that are white in color, its extended flowering season blooming; re-blooming from July to December in South Africa, its very floriferous blooming period producing an unusually high number of inflorescences, its partial resistance to fungal infection from *Macrophoma agapanthii* and its small to medium plant size.

2 Drawing Sheets

Botanical classification: *Agapanthus* hybrid.
Varietal denomination: 'WP001'.

BACKGROUND OF THE INVENTION

The present invention relates to a new and distinct cultivar of *Agapanthus* of hybrid origin and will be referred to hereafter by its cultivar name, 'WP001'. 'WP001' represents a new perennial grown for landscape use.

The new cultivar was derived from a controlled breeding program under the direction of the Inventor in Hartebeespoort, Northwest Province, South Africa. The objective of the breeding program is to develop new cultivars of *Agapanthus* that are fast growing, have early and repeat blooming habits combined with unique flower colors.

The new cultivar arose from a cross made by the Inventor in October of 2007 between unnamed and unpatented proprietary plants of hybrid *Agapanthus* plants from the Inventor's breeding program as the female and male parents. The Inventor selected 'WP001' in November of 2009 as a single unique plant amongst the seedlings that resulted from the above cross.

Asexual propagation of the new cultivar was first accomplished by division by the Inventor in Hartebeespoort, Northwest Province, South Africa in February of 2010. Asexual propagation by division and in vitro propagation has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'WP001' as a distinct cultivar of *Agapanthus*.

1. 'WP001' exhibits a fast growing and fast multiplying growth habit.

2. 'WP001' exhibits inflorescences that form dense umbels of flowers that are white in color.
3. 'WP001' exhibits an extended blooming season; re-blooming from July to December in South Africa.
4. 'WP001' exhibits a very floriferous blooming period by producing an unusually high number of inflorescences.
5. 'WP001' exhibits some resistance to fungal infection from *Macrophoma agapanthii*.
6. 'WP001' exhibits a small to medium plant size.

The female parent of 'WP001' differs from 'WP001' in having a shorter flowering season, in having fewer flowers per inflorescence, and in producing fewer inflorescences. The male parent of 'WP001' differs from 'WP001' in being slower growing, in having a shorter flowering season, in being more susceptible to disease, and in having flowers that are bi-colored. 'WP001' can be most closely compared to the Agapanthus cultivars 'White Storm' (not patented) and 'Snowball' (not patented). Both cultivars are similar to 'WP001' in having a small to medium plant habit and in having flowers that are white in color. 'White Storm' differs from 'WP001' in having inflorescences with taller flowering stems and longer pedicels and in having a shorter blooming period that commences later. 'Snowball' differs from 'WP001' in having inflorescences with taller flowering stems and in having a shorter blooming season that commences later.

BRIEF DESCRIPTION OF THE DRAWINGS

The accompanying colored photographs illustrate the overall appearance and distinct characteristics of the new *Agapanthus*. The photographs were taken of 3 year-old plants (from a division) of 'WP001' as grown outdoors in Linbro Park, Johannesburg, South Africa.

The photograph in FIG. 1 provides a side view of several plants of 'WP001' in bloom.

Figure 1:
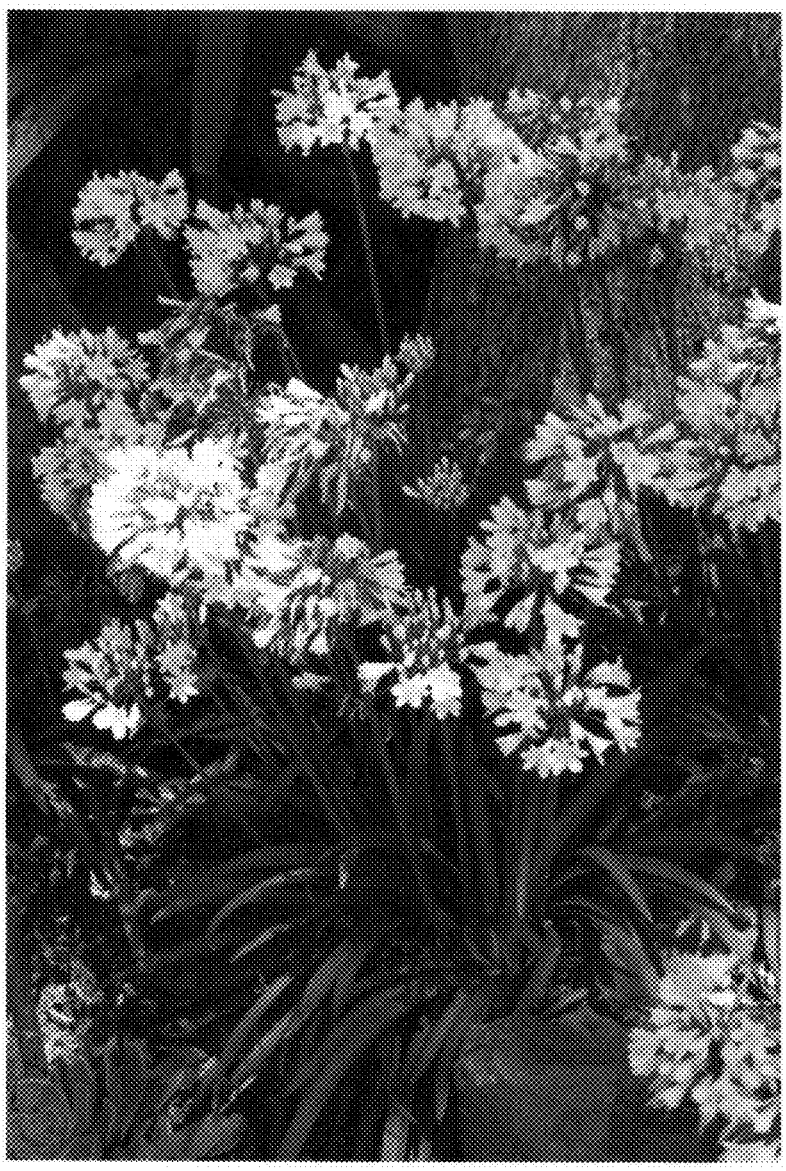
Figure 2:
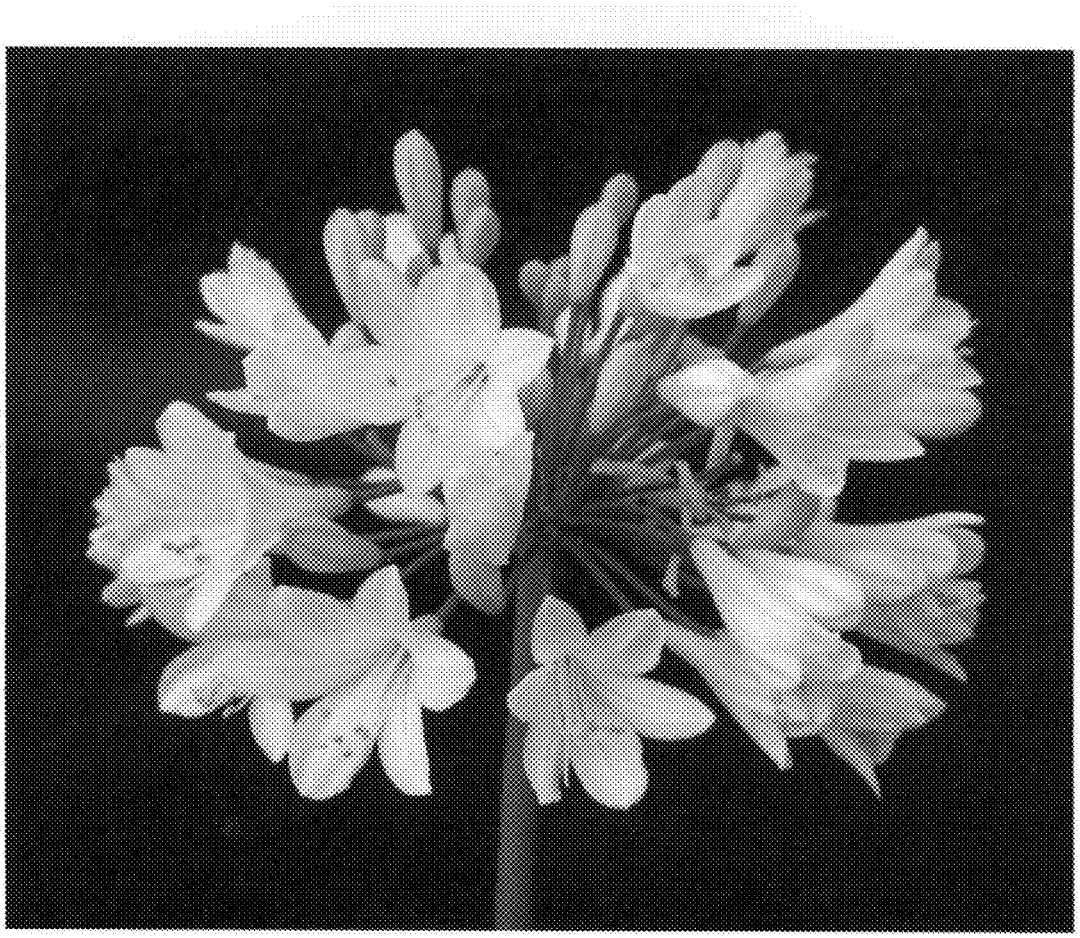

The photograph in FIG. 2 provides a close-up view of an inflorescence of 'WP001'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of one year-old plants (from a division) of 'WP001' as grown in a greenhouse in Loxley, Ala. The phenotype of the new cultivar may vary with variations in environmental, climatic, and cultural conditions, as it has not been tested under all possible environmental conditions. The color determinations are in accordance with The 2007 R.H.S. Colour Chart of The Royal Horticultural Society, London, England, except where general color terms of ordinary dictionary significance are used.

General description:

*Blooming period.*—Re-blooms from July to December with peak bloom in November in South Africa.

*Plant type.*—Semi-deciduous (climate dependent) herbaceous perennial.

*Plant habit.*—Basal rosettes with inflorescences emerging from the rosette center.

*Height and spread.*—30 to 42 cm in height in bloom (foliage height an average of 21 cm) and an average of 35 cm in spread.

*Cold hardiness.*—Some resistance to fungal infections caused by *Macrophoma agapanthii* has been observed.

*Root description.*—Thick and fleshy, primarily 155B in color.

*Propagation.*—Tissue culture and division.

*Growth rate.*—Vigorous.

Foliage description:

*Leaf shape.*—Ligulate.

*Leaf division.*—Simple.

*Leaf base.*—Truncate.

*Leaf arrangement.*—2-ranked.

*Leaf apex.*—Narrowly acute.

*Leaf aspect.*—Emerging leaves erect, then cascade.

*Leaf venation.*—Parallel, color on upper and lower surface matches leaf coloration with the mid rib basal portion of lower surface slightly conspicuous and 144C.

*Leaf margins.*—Entire.

*Leaf size.*—Average of 28 cm in length and 2.3 cm in width when mature.

*Leaf surface.*—Smooth, glabrous, and dull on upper and lower surface.

*Leaf number.*—Average of 18 leaves per rosette 2.5 cm in width at the base.

*Leaf color.*—Young leaves upper and lower surface; a blend of 144A to 144C and blending to 137C near apex and 157D at base, mature leaves upper and lower surface; a blend of 137A and N137A and 157C at base.

*Leaf attachment.*—Sessile to base.

Flower description:

*Inflorescence type.*—Dense, full umbel.

*Flower fragrance.*—None.

*Flower type.*—Rotate, campanulate, base of tepals fused.

*Flower number.*—An average of 85 flowers per umbel.

*Inflorescence size.*—Average of 14 cm in height and 9 cm in diameter (when flowers are half open).

*Flower size.*—An average of 3 cm in depth and 3 cm in diameter.

*Lastingness of inflorescence.*—Average of 2 weeks.

*Flower aspect.*—Outward to slightly downward from the pedicle.

*Peduncle.*—1 to 2 per rosette with rebloom, very strong, slightly oval in shape, held at an average angle of 0° to 15° (upright=0°), average of 30 cm in length and 1 cm in width at distal region and 6 mm in width at proximal region, a blend of 137C and 138A in color, satiny, glabrous and slightly glaucous surface.

*Pedicels.*—Very strong, average of 3 cm in length and 1.5 mm in width, held erect to outward (0° to 180°), color 144A.

*Flower buds.*—Obelliptic in shape, average of 2.5 cm in length and 8.5 mm in width, NN155A in color with slight stripes of 144C.

*Inflorescence bract.*—Deciduous spathe-like enclosing inflorescence prior to opening, ovate in shape, acuminate apex, truncate base, an average of 3.5 cm in width and 1.7 cm in width, color outer and inner surface; a blend of 144A, 144B and 137D, outer surface glabrous and satiny, inner surface glabrous and dull.

*Tepals.*—6 (3 inner and 3 outer), rotate, obelliptic in shape, lower 30% fused (tube portion 1 cm in length and 5 mm in width, entire margins, broadly acute apex, glabrous on all surfaces, inner and outer tepals are an average of 3 cm in length and 1.2 cm in width (near apex), both surfaces of inner and outer tepals are NN155C in color with a light tinge of 157B on the midrib of the lower surfaces.

Reproductive organs:

*Gynoecium.*—1 pistil, stigma is disk-shaped shaped, 0.5 mm in length, and 157C in color, style is 22 cm in length and NN155C in color, ovary is oblong in shape, 1 cm in length, 2.5 mm in width and 145A in color.

*Androcoecium.*—6 stamens, anthers are dorsified, irregularly oblong in shape, average of 1.5 mm in length, and 7B in color, filament is 2.5 cm in length, 1 mm in width, and NN155C in color, lower 7 mm in adnate to inner surfaces of tepals, pollen is abundant in quantity and 15A in color.

*Fruit/seed.*—Have not been observed.

It is claimed:

1. A new and distinct cultivar of *Agapanthus* plant named 'WP001' as herein illustrated and described.

* * * * *